United States Patent [19]

Walker, deceased

[11] 4,337,365
[45] Jun. 29, 1982

[54] PROCESS FOR THE SELECTIVE HYDROFORMYLATION OF METHANOL TO ACETALDEHYDE

[75] Inventor: Wellington E. Walker, deceased, late of Sissonville, W. Va., by Maxine M. Walker, administratrix

[73] Assignee: Union Carbide Corporation, Danbury, Conn.

[21] Appl. No.: 233,971

[22] Filed: Feb. 17, 1981

Related U.S. Application Data

[63] Continuation-in-part of Ser. No. 138,678, Apr. 9, 1980, abandoned.

[51] Int. Cl.$^3$ .................. C07C 45/49; C07C 47/06
[52] U.S. Cl. .................................... 568/487; 568/449
[58] Field of Search ........................... 568/487, 449

[56] References Cited

U.S. PATENT DOCUMENTS 4,151,208 4/1979 Pretzer et al. .
4,225,517 9/1980 Gane ................................. 568/487
4,239,925 12/1980 Pretzer et al. .................... 568/487

FOREIGN PATENT DOCUMENTS 78300607.5 10/1979 European Pat. Off. .
48-02525 1/1973 Japan ............................... 568/487
52-136111 11/1977 Japan .

Primary Examiner—Werren B. Lone
Attorney, Agent, or Firm—Francis M. Fazio

[57] ABSTRACT

A process for the production of acetaldehyde from the cobalt-catalyzed, iodide-promoted reaction of methanol, hydrogen and carbon monoxide, attaining (a) selectivity to acetaldehyde heretofore unachievable and (b) high methanol conversion, wherein the reaction is carried out in an inert solvent at a temperature of from 100° C. to 180° C. with an iodide to cobalt mole ratio of from 2:1 to 100:1.

13 Claims, No Drawings

PROCESS FOR THE SELECTIVE HYDROFORMYLATION OF METHANOL TO ACETALDEHYDE

This application is a continuation-in-part of application Ser. No. 138,678, filed on Apr. 9, 1980, abandoned.

BACKGROUND OF THE INVENTION

Acetaldehyde is a very useful chemical compound and is of considerable importance as an intermediate in the production of acetic acid, acetic anhydride, ethyl acetate, acetone, acetal resins and other derivatives.

Acetaldehyde can be produced by a number of chemical processes such as the dehydrogenation of ethanol or the hydration of acetylene. Another route to acetaldehyde is the cobalt catalyzed reaction of methanol with hydrogen and carbon monoxide. However, this method has been plagued with poor selectivity to acetaldehyde. U.S. Pat. No. 4,151,208 discloses improved selectivity to acetaldehyde by including an iodine promoter with the cobalt catalyst in the methanol, hydrogen, carbon monoxide reaction. Although some improvement is shown over the theretofore available processes the selectivity to acetaldehyde was only from 50–60 percent and the methanol conversion only from 50–70 percent.

Other catalyst systems have been employed to catalyze the reaction. For example European patent application Ser. No. 78 30 0607 discloses a process employing an inert liquid and a catalyst of cobalt, iodide or bromide, and arsenic, antimony or bismuth. Japanese Publication No. JA/77/-13611 discloses a process catalyzed by cobalt, a halogen, and phosphorus. Since the reactants, methanol, hydrogen and carbon monoxide are relatively inexpensive and plentiful any process which can facilitate their reaction to acetaldehyde would be very desirable. It would also be highly desirable for the catalyst for this reaction to be a simple and inexpensive as possible. Therefore a process which would improve the conversion and the selectivity of the cobalt-catalyzed, iodide-promoted reaction of methanol, hydrogen and carbon monoxide to selectively produce acetaldehyde would be of great advantage.

SUMMARY OF THE INVENTION

It has now been found that cobalt-catalyzed, iodide-promoted reaction of methanol, hydrogen and carbon monoxide will produce acetaldehyde at a selectivity of from 70 to 80 percent at a methanol conversion of from 80 to 90 percent, results, heretofore unachievable by known methods, when the reaction is carried out in certain inert solvents at a temperature of from 100° C. to 180° C. and a mole ratio of iodide to cobalt of from 2:1 to 100:1.

DESCRIPTION OF THE INVENTION

This invention is an improved catalytic method for selectively producing acetaldehyde from methanol, hydrogen and carbon monoxide. Furthermore, any compounds which will form hydrogen and carbon monoxide, such as the mixture of water and carbon monxide or the mixture of hydrogen and carbon dioxide, can be used as a substitute for the mixture of hydrogen and carbon monoxide used herein to exemplify the present invention.

In the process of this invention the reaction is run in a substantially inert solvent; the presence of the inert solvent being critical to the attainment of high acetaldehyde selectively at high methanol conversion. Any inert solvent which does not inhibit the hydroformylation reaction can be used in the improved process of this invention and illustrative thereof one can name dioxane, toluene, tetrahydrofuran, the dimethyl ether of tetraethylene glycol, 1,2-dimethoxybenzene, and the like. The preferred solvent is dioxane. The inert solvent is present in a volume ratio of solvent to methanol of from about 0.5:1 to about 100:1; preferably from about 1:1 to about 10:1, most preferably from about 1:1 to about 3:1.

The temperature at which the reaction is carried out is critical for the selective production of acetaldehyde and can vary from 100° C. to 180° C.; preferably from 120° C. to 160° C.

The reaction pressure can vary from 1000 psig to 10000 psig or higher, preferably from 2000 psig to 7000 psig.

The mole ratio of hydrogen to carbon monoxide is from 1:10 to 10:1; the preferred being from about 1:1 to about 4:1.

The catalyst system for the improved hydroformylation process of this invention contains a cobalt catalyst and an iodine or iodide promoter. The cobalt-iodide catalyst system is present in a catalytically effective amount, sufficient to catalyze the reaction, preferably from 1.5 to 35 weight percent, most preferably from 10 to 20 weight percent, based on the amount of methanol present.

The cobalt component of the catalyst system can be furnished from a number of sources, for example, any of the known cobalt carboxylates such as cobalt formate, cobalt acetate, cobalt propionate, cobalt butyrate, cobalt valerate, cobalt hexanoate, and the like; the known cobalt carbonyl compounds such as dicobalt octacarbonyl, methyl cobalt tetracarbonyl, acetyl cobalt tetracarbonyl, and the like, or their phosphine substituted analogs many of which are known to those skilled in the art; cobalt oxide and cobalt hydroxide, cobalt carbonate and cobalt bicarbonate; and the soluble cobalt halides such as cobalt iodide, cobalt bromide and cobalt chloride. A convenient source of cobalt is cobalt acetate.

The mole ratio of cobalt to methanol can be from 1:5 to 1:20,000 preferably from 1:50 to 1:500.

The iodide promoter of the catalyst system can come from any iodine-containing source which is capable of ionizing so as to supply iodide ion to the reactor. Illustrative as sources of the iodide atom are elemental iodine; cobalt iodide, potassium iodide, lithium iodide, hydrogen iodide, the alkyl iodides having from 1 to 10 carbon atoms such as methyl iodide, propyl iodide, 2-ethylhexyl iodide, n-decyl iodide, and the like, the organic ammonium iodides of the formula $R_4NI$ and the organic phosphonium iodides of the formula $R_4PI$ wherein R is alkyl having from 1 to 10 carbon atoms or aryl having from 6 to 10 ring carbon atoms such as tetramethyl ammonium iodide, tetraethyl ammonium iodide, tetraethylhexyl ammonium iodide, tetraphenyl ammonium iodide, tetramethyl phosphonium iodide, tetrapropyl phosphonium iodide, tetraethylhexyl phosphonium iodide, tetraphenyl phosphonium iodide and the like. The preferred source of the iodide is elemental iodine.

The mole ratio of iodide to cobalt in the catalyst mixture is critical for the selective production of acetaldehyde by use of the improved process of this invention. The mole ratio of iodide to cobalt is from 2:1 to 100:1, preferably it is from 2:1 to 20:1, most preferably from 4:1 to 8:1.

The reaction time will vary and is dependent on batch size, other reaction parameters employed and the specific components used in the cobalt-iodide catalyst system.

In a typical embodiment of a laboratory scale batch process, methanol is charged to a reactor with the inert solvent and a catalyst system containing a cobalt compound and an iodine compound; the reactor is purged charged with the hydrogen/carbon monoxide gas mixture, sealed and heated until the desired reaction is completed. It is well known that commercially this process could be run continuously.

The improved process of this invention allows for the selective production of acetaldehyde from the reaction of methanol, hydrogen and carbon monoxide, at a methanol conversion and acetaldehyde selectivity heretofore simultaneously unachievable by the processes known to those skilled in the art. By use of the improved process of this invention, acetaldehyde, a valuable intermediate for many chemicals, can be produced significantly more economically than was heretofore possible. This highly advantageous result was unexpected and could not have been predicted.

The following examples serve to further illustrate the improved process of this invention. In these examples and in the experiments which also follow methanol conversion is calculated as (grams MeOH charged-grams MeOH discharged)/(grams MeOH charged X 100) and selectivity is calculated as (grams AcH/grams total product by 100). Further, the following abbreviations are used:

| MeOH | Methanol |
|------|----------|
| AcH | acetaldehyde |
| EtOH | ethanol |
| MeOAc | methyl acetate |
| AcOH | acetic acid |
| DMAc | dimethyl acetal |
| EtOAc | ethyl acetate |
| PrH | propionaldehyde |

EXAMPLE 1

There were charged to a 316 stainless steel lined 250 cc autoclave 30 ml of reagent grade methanol, 60 ml of dioxane, 6 millimoles of cobalt acetate and 12 millimoles elemental iodine. The reactor was sealed, purged with carbon monoxide and then pressurized to 3000 psig with a gaseous mixture having a 2:1 molar ratio of hydrogen to carbon monoxide. The reactor and its contents were heated at 160° C. for three hours during which the reactor contents were stirred to obtain thorough mixing. During the reaction the average reaction pressure was about 3500 psig. After this three hour period the reactor was cooled to 0°–5° C. and vented, and the liquid reaction product mixture was recovered and analyzed using a vapor phase gas chromatograph equipped with a thermal conductivity detector and a ⅛ inch by 6 foot column packed with a commercially available polystyrene resin commonly used for gas chromatography.

The selectivity of the reaction to acetaldehyde was 67 percent and the conversion of methanol was 89 percent. This example clearly demonstrates the significantly improved results obtained by use of the improved process of this invention over typical heretofore achievable results as indicated, for example, in U.S. Pat. No. 4,151,208.

EXAMPLE 2

A procedure similar to that described in Example 1 was used in this series of five runs. In each run 20 cc of methanol and 60 cc of dioxane were charged and the hydroformylation was carried out at 3500 psig with a gaseous mixture having a 2:1 molar ratio of hydrogen to carbon monoxide. The cobalt was introduced in the form of cobalt acetate and the iodide was introduced in the form of elemental iodine. Each run was carried out at the temperature and for the duration indicated in Table 1. The reaction product mixture was analyzed by the method employed in Example 1 and the results are reported in Table 1.

TABLE I

| Run | Co mmoles | I$_2$ mmoles | Mole Ratio I:Co | Temp. (°C.) | Time (hrs) | % MeOH Conversion | Selectivity (%) | | | | |
|-----|-----------|--------------|-----------------|-------------|------------|-------------------|------|------|-----|-------|------|
| | | | | | | | AcH | EtOH | PrH | MeOAc | DMAc |
| 1 | 6 | 12 | 4:1 | 160 | 2 | 82 | 72 | 2.9 | — | 11.6 | 13.5 |
| 2 | 6 | 12 | 4:1 | 140 | 5 | 93 | 74.5 | 3.3 | 1.7 | 6 | 14.5 |
| 3 | 6 | 12 | 4:1 | 120 | 5 | 77 | 68.5 | — | — | 10.5 | 21 |
| 4 | 3 | 12 | 8:1 | 160 | 3 | 84 | 73.4 | 2.8 | — | 7.7 | 16.1 |
| 5 | 3 | 12 | 8:1 | 140 | 5 | 88 | 75.8 | 3.8 | 1.2 | 5.1 | 14.1 |

The results further demonstrate the high selectivity and methanol conversion achieved by the improved process of this invention. The results of each of the five runs significantly exceeded the results reported for the process of U.S. Pat. No. 4,151,208 for both methanol conversion and acetaldehyde selectivity. Of particular interest are the results of Run 3; here, even at a temperature far lower than the lower limit of this prior art process, both the conversion and selectivity exceeded that of the known process. This further exemplifies the significant improvement in methanol conversion and acetaldehyde selectivity achieved by the process of this invention over that achievable by heretofore known methods.

EXAMPLE 3

A procedure similar to that described in Example 1 was used in this series of three runs. In each run 20 cc of methanol, 60 cc of dioxane, 3 mmoles of cobalt acetate and 12 mmoles of elemental iodine, giving an iodide; cobalt mole ratio of 8:1 were charged, with the hydroformylation carried out at 140° C. for three hours at an average pressure of about 6000 psig with the hydrogen to carbon monoxide mole ratios indicated in Table II. The reaction product mixtures were analyzed by the method employed in Example 1 and the results are reported in Table II.

TABLE II

| Run | Mole Ratio H$_2$:CO | % MeOH Conversion | Selectivity (%) | | | | |
|-----|---------------------|-------------------|------|------|-----|-------|------|
| | | | AcH | EtOH | PrH | MeOAc | DMAc |
| 1 | 4:1 | 80 | 71 | 1.9 | 1 | 6.1 | 20 |
| 2 | 3:2 | 88 | 79.5 | 2.3 | 1 | 6.5 | 10.7 |
| 3 | 1:1 | 87 | 77.5 | 1 | 0.5 | 11 | 10 |

The results demonstrate that the improved hydroformylation process of this invention to selectivity produce acetaldehyde is effective at higher pressures and over a wide range of hydrogen to carbon monoxide mole ratios.

EXAMPLE 4

A procedure similar to that described in Example 1 was used in this series of four runs. In each run 20 cc of methanol and 60 cc of dioxane were charged and reacted at 140° C. for 3 hours at an average pressure of about 6000 psig with a hydrogen to carbon monoxide mole ratio of 3:2. Each run contained 3 mmoles of cobalt acetate and the source of iodide was varied; however, in all runs the I:Co mole ratio was 8:1. The reaction product mixture was analyzed by the method employed in Example 1 and the results are reported in Table III.

TABLE III

| Run | I (mmoles, source) | | % MeOH Conversion | AcH | EtOH | PrH | MeoAc | DMAc |
|---|---|---|---|---|---|---|---|---|
| 1 | 12, | $I_2$ | 84 | 81.1 | 3.9 | 1.1 | 4.8 | 9.1 |
| 2 | 24, | KI | 65 | 47.1 | 1.5 | 2.5 | 8.1 | 40.8 |
| 3 | 24, | HI* | 88 | 82.1 | 2.4 | 1 | 5.4 | 9.1 |
| 4 | 24, | $CH_3I$ | 81 | 79.6 | 2.4 | 1.6 | 7.1 | 9.3 |

*added to 57 percent aqueous solution

The results demonstrate that the improved hydroformylation process of this invention can utilize iodide ion from several sources, although as the results of run 2 indicate, the improved process of this invention is less selective when potassium iodide is the source of the iodide promoter.

EXAMPLE 5

The procedure described in Example 1 was repeated except that the mole ratio of hydrogen to carbon monoxide was 1:1 and the amounts of methanol and dioxane were both 40 ml. For comparative purposes the above procedure was repeated without the inert dioxane solvent; in this comparative run there was employed 80 ml of methanol, 8 mmoles of cobalt acetate and 16 mmoles of elemental iodine—thus the I:Co mole ratio was 4:1, the same as above. In both runs the reaction mixture was sampled periodically. The results of the run employing solvent are shown in Table IV and the results of the comparative run are shown in Table V. In Table V the products listed as HEAVIES were higher molecular weight oxygenated products such as aldehydes, esters and alcohols containing more than 4 carbon atoms.

TABLE IV

| Time | % MeOH Conversion | Selectivity (%) | | | | |
|---|---|---|---|---|---|---|
| | | AcH | EtOH | MeOAc | DMAc | AcOH |
| 15 min. | 47 | 43.1 | — | 21.2 | 35.7 | — |
| 30 min. | 55 | 55.2 | 1.6 | 23.3 | 19.9 | — |
| 1 hr. | 71 | 59.8 | 1.8 | 25.0 | 13.4 | — |
| 1.5 hrs. | 82 | 53.3 | 2.2 | 22.9 | 13.3 | 8.4 |
| 3 hrs. | 90 | 46.7 | 1.9 | 17.0 | 16.1 | 18.3 |

TABLE V

| Time | % MeOH Conversion | Product Distribution (%) | | | | | |
|---|---|---|---|---|---|---|---|
| | | AcH | EtOH | MeOAC | DMAc | AcOH | HEAVIES |
| 10 min. | 35 | 24.8 | — | 25.8 | 45.4 | — | 4.0 |
| 30 min. | 50 | 25.3 | — | 31.8 | 29.2 | — | 3.8 |
| 1 hr. | 59 | 37.9 | 1.3 | 37.4 | 18.8 | — | 4.6 |
| 1.5 hrs. | 68 | 34.8 | 1.4 | 36.1 | 15.2 | 6.5 | 6.0 |
| 2 hrs. | 72 | 31.8 | 1.7 | 35.4 | 12.8 | 11.7 | 6.6 |
| 3 hrs. | 78 | 25.7 | 1.4 | 32.3 | 12.4 | 19.9 | 8.3 |
| 4 hrs. | 81 | 22.1 | 1.5 | 29.3 | 12.7 | 24.8 | 9.6 |
| 5 hrs. | 86 | 17.9 | 1.4 | 28.6 | 13.2 | 22.8 | 16.1 |

The results demonstrate the very beneficial effect the inert solvent has in the improved process of this invention. Under virtually identical reaction conditions, the presence of the inert solvent resulted in an increase in both methanol conversion and acetaldehyde selectivity over that observed when the inert solvent was not employed. For example, after 3 hours of reaction the increase in methanol conversion was 15 percent and the increase in acetaldehyde selectivity was 82 percent for the run with inert solvent over that without inert solvent.

COMPARATIVE EXPERIMENT A

A series of ten runs was carried out using a procedure similar to that described in Example 1 except that the inert solvent was not employed and each run was carried out with a 60 cc charge of methanol. In each run the cobalt source was cobalt acetate tetrahydrate. The other reaction conditions are shown in Table VI. The reaction products of each run were analyzed as in Example 1 and the results are reported in Table VI.

TABLE VI

| Run | Co mmoles | I mmoles, source | | Mole Ratio (I:Co) | Total Pressure (psig) | Mole Ratio ($H_2$:CO) | Temp. (°C.) | Time (hrs) | % MeOH Conversion | Selectivity % | | | | | |
|---|---|---|---|---|---|---|---|---|---|---|---|---|---|---|---|
| | | | | | | | | | | AcH | EtOH | MeOAc | AcOH | DMAc+ EtOAc | HEAVIES |
| 1 | 6 | 6, | LiI | 1:1 | 2000 | 1:1 | 190 | 5 | 79 | 5.2 | 28.3 | 24.4 | 6.5 | 19.5 | 16.1 |
| 2 | 6 | 3, | $I_2$ | 1:1 | 2000 | 1:1 | 190 | 5 | 89 | 4.1 | 21.7 | 16 | 20.8 | 19.1 | 18.3 |
| 3 | 6 | 18, | LiI | 3:1 | 2000 | 1:1 | 190 | 5 | 92 | 7.6 | 14.4 | 15.9 | 25 | 19.9 | 17.2 |
| 4 | 6 | 18, | LiI | 3:1 | 2000 | 1:1 | 160 | 5 | 84 | 19.3 | 6.2 | 25 | 20.3 | 15.7 | 13.5 |
| 5 | 6 | 12, | $I_2$ | 4:1 | 2000 | 1:1 | 160 | 5 | 89 | 17.8 | 1 | 30.8 | 26.1 | 13 | 11.3 |

TABLE VI-continued

| Run | Co mmoles | I mmoles, source | Mole Ratio (I:Co) | Total Pressure (psig) | Mole Ratio (H$_2$:CO) | Temp. (°C.) | Time (hrs) | % MeOH Conversion | Selectivity % |  |  |  |  |  |
|---|---|---|---|---|---|---|---|---|---|---|---|---|---|---|
|  |  |  |  |  |  |  |  |  | AcH | EtOH | MeOAc | AcOH | DMAc+ EtOAc | HEAVIES |
| 6 | 6 | 12,I$_2$ | 4:1 | 3000 | 1:1 | 160 | 2 | 74 | 34.6 | 1.2 | 33.4 | 1.3 | 20.6 | 7.2 |
| 7 | 6 | 24,HI | 4:1 | 2000 | 1:1 | 160 | 3 | 73 | 28.4 | 0.5 | 38.5 | 6.9 | 20.3(a) | 5.4 |
| 8 | 6 | 24,KI | 4:1 | 3000 | 1:1 | 160 | 2 | 64 | 21.6 | 1.2 | 37.4 | — | 35.6(a) | 4.2 |
| 9 | 6 | 12,I$_2$ | 4:1 | 3000 | 2:1 | 140 | 5 | 70 | 32.6 | 0.8 | 32 | — | 25.1(a) | 9.4 |
| 10 | 6 | 24,HI | 4:1 | 3000 | 2:1 | 160 | 3 | 59 | 32.7 | 1 | 24.3 | — | 35.3(a) | 6.8 |

(a)DMAc only

The results demonstrate the general overall poor selectivity to acetaldehyde obtained when the process of this invention is not employed. The products listed as HEAVIES in the table were the same as those in Example 5. As is shown, the data establishes that when the improved process of this invention is not used a wide variety of products are obtained but one does not achieve high selectivity to acetaldehyde. Further, as the reaction conditions are altered in attempts to increase the acetaldehyde selectivity, there is generally observed a decrease in methanol conversion. Runs 1 and 2, in which none of the three critical criteria of the improved process of this invention are employed, display the worst results, although methanol conversions are quite high, selectivity to acetaldehyde was very poor in both runs. This further demonstrates the criticality of the three parameters (presence of inert solvent, specific temperature range, and specific iodide/cobalt ratio) found critical for the improved process of this invention. Though Runs 4–10 were conducted at temperatures within the range found desirable in this process and using I:Co ratios also within the desired range, low selectivity to acetaldehyde was noted due to the absence of the inert solvent.

COMPARATIVE EXPERIMENT B

For comparative purposes there was conducted a run using a procedure similar to that of Example 1 except that the reaction temperature was outside the critical range. To the reactor were charged 20 ml of methanol, 60 ml of dioxane, 12 mmoles of elemental iodine and 3 mmoles of cobalt acetate to give an I:Co mole ratio of 8:1; the hydroformylation was carried out at about 3500 psig with a gaseous mixture having a 2:1 molar ratio of hydrogen to carbon monoxide and at a reaction temperature of 190° C. After 3 hours of reaction the reaction product mixture was analyzed by the method employed in Example 1. The results are shown in Table VII.

TABLE VII

| % MeOH Conversion | Product Distribution (%) | | | |
|---|---|---|---|---|
|  | AcH | EtOH | PrH + MeOAc | EtOAc |
| 98 | 49.3 | 23.3 | 8.2 | 19.2 |

The results demonstrate that the temperature range is critical to the attainment of high acetaldehyde selectivity at high methanol conversion; although the methanol conversion was quite high the selectivity to acetaldehyde was low when the reaction temperature was above the critical range.

COMPARATIVE EXPERIMENT C

For comparative purposes there was conducted a run using a procedure similar to that of Example 1 except that the I:Co mole ratio was outside the critical range. To the reactor were charged 20 ml of methanol; 60 ml of dioxane, 3 mmoles of elemental iodine and 6 mmoles of cobalt acetate to give an I:Co mole ratio of 1:1; the hydroformylation was carried out at about 3500 psig with a gaseous mixtures having a 2:1 molar ratio of hydrogen to carbon monoxide, and at a reaction temperature of 160° C. After 4 hours of reaction the reaction product mixture was analyzed by the method employed in Example 1. The results are shown in Table VIII.

TABLE VIII

| % MeOH Conversion | Product Distribution (%) | | | | |
|---|---|---|---|---|---|
|  | AcH | EtOH | PrH | MeOAc | DMAc |
| 72 | 48.7 | 19.7 | 3.4 | 10.2 | 17.9 |

The results demonstrate that the I:Co mole ratio is critical to the attainment of high acetaldehyde selectivity at high methanol conversion; although the methanol conversion was acceptable the selectivity to acetaldehyde was low when the I:Co mole ratio was below the critical range.

The results of the examples and the comparative experiments establish the critical relationship of the three parameters found necessary by applicant, namely, the need for an inert solvent, an I:Co mole ratio of from 2:1 to 100:1 and a reaction temperature of from 100° C. to 180° C. Under these limited and critical conditions one achieves both high methanol conversion and high selectivity to the formation of acetaldehyde during the hydroformylation reaction of methanol with hydrogen and carbon monoxide. The data clearly establishes that deviation from these conditions precludes one from obtaining both.

The presence of inert solvent by itself does not lead to high acetaldehyde selectivity at high methanol conversion; neither does the critical reaction temperature, by itself, nor does the critical I:Co mole ratio by itself. Furthermore, no two of these critical parameters without the third will give high acetaldehyde selectivity at high methanol conversion. Thus, if one runs at proper temperature and I:Co ratio but with no solvent, poor selectivity is the result; if one runs with solvent at proper temperature but at an I:Co ratio outside the critical limits poor selectivity is observed; if one runs with solvent and proper I:Co mole ratio but at a temperature outside the critical limits, poor selectivity results. No one critical parameter is controlling nor do any two in combination give good results. Only when all three critical parameters are present within the defined limits and acting in concert is the high acetaldehyde selectivity at high methanol conversion attained. It is completely unobvious why this should be so. There is an unobvious synergistic effect when all three critical parameters are employed. When any one of these parameters is missing the results obtained are poor. The beneficial synergistic effect obtained when all three critical parameters are present is entirely unobvious and could not have been predicted from the known prior art.

What is claimed is:

1. In a process for selectively producing acetaldehyde from the reaction of methanol, hydrogen and carbon monoxide at a pressure of from 1,000 psig to 10,000 psig and a $H_2:CO$ mole ratio of from 1:10 to 10:1 and wherein the reaction is catalyzed by a catalyst system consisting essentially of cobalt and iodide, the improvement consisting of carrying out the reaction at a temperature of from 100° C. to 180° C. in the presence of a substantially inert solvent from the group of dioxane, tetrahydrofuran, the dimethyl ether of tetraethylene glycol and 1,2-dimethoxybenzene at an iodide to cobalt mole ratio of from 2:1 to 100:1 and wherein the volume ratio concentration of said inert solvent to methanol is from 0.5:1 to 100:1.

2. The improved process as claimed in claim 1 wherein said temperature is from 120° C. to 160° C.

3. The improved process as claimed in claim 1 wherein the said inert solvent is present in a volume ratio of from 0.5:1 to 100:1 based on the volume of methanol present.

4. The improved process as claimed in claim 3 wherein said volume ratio is from 1:1 to 10:1.

5. The improved process as claimed in claim 3 wherein said volume ratio is from 1:1 to 3:1.

6. The improved process as claimed in claim 1 wherein said inert solvent is dioxane.

7. The improved process as claimed in claim 1 wherein the mole ratio of iodide to cobalt is from 2:1 to 20:1.

8. The improved process as claimed in claim 1 wherein the mole ratio of iodide to cobalt is from 4:1 to 8:1.

9. The improved process as claimed in claim 1 wherein the cobalt-iodide catalyst system is present at from 1.5 weight percent to 35 weight percent, based on the amount of methanol present.

10. The improved process as claimed in claim 1 wherein the cobalt-iodide catalyst system is present at from 10 to 20 weight percent, based on the amount of methanol present.

11. The improvement process as claimed in claim 1 wherein the source of cobalt is cobalt acetate.

12. The improved process as claimed in claim 1 wherein the source of iodide is elemental iodine.

13. The improved process as claimed in claim 1 wherein the source of iodide is selected from the group comprising hydrogen iodide and methyl iodide.

* * * * *